United States Patent [19]

Fitzgerald et al.

[11] Patent Number: 4,524,610
[45] Date of Patent: Jun. 25, 1985

[54] IN-LINE VIBRATORY VISCOMETER-DENSITOMETER

[75] Inventors: J. Vincent Fitzgerald, Metuchen; Frank J. Matusik, Piscataway; Donald W. Nelson, Voorhees, all of N.J.

[73] Assignee: National Metal and Refining Company, Ltd., Edison, N.J.

[21] Appl. No.: 528,744

[22] Filed: Sep. 2, 1983

[51] Int. Cl.³ .............................................. G01N 11/16
[52] U.S. Cl. ...................................... 73/54; 73/32 A; 73/59
[58] Field of Search .................... 73/59, 54, 32 A, 179, 73/60, 702

[56] References Cited

U.S. PATENT DOCUMENTS

| | | | |
|---|---|---|---|
| 2,839,917 | 6/1958 | Roth et al. | 73/59 |
| 2,943,476 | 7/1960 | Bernstein | 73/32 A |
| 3,177,705 | 4/1965 | Banks | 73/59 |
| 3,382,706 | 5/1968 | Fitzgerald et al. | 73/59 |
| 3,710,614 | 1/1973 | Oppliger | 73/59 |
| 3,712,117 | 1/1973 | Fitzgerald et al. | 73/59 |
| 3,762,429 | 10/1973 | Fitzgerald et al. | 137/92 |
| 4,217,774 | 8/1980 | Agar | 73/32 A |

FOREIGN PATENT DOCUMENTS 401908  2/1984  U.S.S.R. .............................. 73/32 A

Primary Examiner—Stewart J. Levy
Assistant Examiner—Hezron E. Williams
Attorney, Agent, or Firm—Arthur L. Lessler

[57] ABSTRACT

A rotational vibratory viscometer-densitometer for in-line process control and similar applications, having an elastic hollow metal tube extending between two clamps, and a relatively rigid transverse yoke secured to the tube at a point midway between the clamps. The yoke has magnetically permeable ends and a magnetically permeable center portion. Electromagnets adjacent one end of the yoke and the center portion thereof interact with the yoke to cause the tube to oscillate simultaneously in torsion and in flexure at the natural frequency of the tube in combination with the fluid within it. The amplitude of torsional oscillation is maintained constant by a torsional detector and control circuit, and the power required to maintain said amplitude is determined, said power being a measure of the viscosity of the fluid flowing through the tube. The frequency of flexural oscillation of the tube is determined by a flexural detector and associated circuit, said frequency being a measure of the density of the fluid flowing through the tube.

24 Claims, 11 Drawing Figures

IN-LINE VIBRATORY VISCOMETER-DENSITOMETER

BACKGROUND OF THE INVENTION

This invention relates to an improved vibratory viscometer transducer and circuit for measuring the viscosity of fluids, which is particularly suitable for, but not limited to in-line process control applications; and to an in-line instrument capable of measuring both the viscosity and the density of a fluid.

Rotational vibratory viscometers are well known in the art, and generally comprise (i) a transducer having a tip immersible in a fluid the viscosity of which is to be determined, (ii) an electromagnetic drive coil for causing the tip to rotationally oscillate with a very small angular amplitude, (iii) a feedback control circuit for maintaining the angular amplitude of oscillation of the tip at a predetermined constant value irrespective of the viscosity of the fluid, and (iv) a circuit for determining the power supplied to the drive coil, usually by squaring the current supplied to said coil, which power is a measure of the viscosity of the fluid.

A viscometer of this type is described, for example, in "Viscometer for Energy Saving", J. V. Fitzgerald, F. J. Matusik, and P. C. Scarna, Jr., Measurements & Control April 1980. Similar viscometers are described in the references cited in said article, as well as in U.S. Pat. Nos. 3,382,706; 3,710,614; 3,712,117; 3,672,429; 3,875,791; and 4,299,119; and in copending U.S. patent application Ser. No. 483,142, filed Apr. 8, 1983 and assigned to the assignee of the present application.

Such viscometers, however, are not well suited for in-line process control applications where the viscosity of a fluid flowing in a pipe has to be continuously monitored, in that the prior art vibratory viscometers require immersion of the transducer tip in the fluid stream, resulting in undesirable turbulence and restriction of flow. In cases where the fluid stream contains suspended particles, these tend to build up on the viscometer tip, altering its characteristics. Further, since vibratory viscometers inherently measure the viscosity-density product of the fluid, in order to determine actual viscosity it is necessary to determine the density of the fluid; and prior art vibratory viscometers require either a manually set density input or a signal from a separate densitometer.

Accordingly, an object of the present invention is to provide an improved vibratory viscometer transducer and circuit suitable for in-line process control applications.

SUMMARY OF THE INVENTION

As herein described, there is provided a transducer assembly for an in-line vibratory viscometer, comprising: a tube exhibiting elasticity; means for securing first and second longitudinally spaced sections of said tube to provide oscillation nodes at said sections; a transverse yoke secured to a third section of said tube intermediate said first and second sections thereof; drive means comprising means operatively associated with said yoke for exciting and maintaining oscillation of said tube between said nodes; and detector means for detecting said oscillation.

Also herein described is a transducer assembly for an in-line vibratory viscometer, comprising: a tube exhibiting elasticity; means for securing first and second longitudinally spaced sections of said tube to provide oscillation nodes at said sections; a transverse yoke secured to a third section of said tube intermediate said first and second sections thereof; drive means comprising means operatively associated with said yoke for exciting and maintaining oscillation of said tube between said nodes, said drive means comprising: flexural drive means for causing said tube to flexurally oscillate in deflection about the longitudinal axis of the tube, torsional drive means for causing said tube to rotationally oscillate in torsion about said longitudinal axis, flexural detector means responsive to the flexural oscillation of said tube, and torsional detector means responsive to the torsional oscillation of said tube.

According to another aspect of the invention there is provided an in-line vibratory viscometer, comprising: a transducer having: a tube exhibiting elasticity, means for securing first and second longitudinally spaced sections of said tube to provide oscillation nodes at said sections, a transverse yoke secured to a third section of said tube intermediate said first and second sections thereof, drive means comprising means operatively associated with said yoke for exciting and maintaining torsional oscillation of said tube between said nodes, and detector means for detecting said torsional oscillation; first circuit means connected between said drive means and said detector means for providing a torsional oscillation mode control signal to said drive means to maintain said tube in torsional oscillation at substantially the natural frequency thereof and at a predetermined constant amplitude; and second circuit means coupled to said drive means and said detector means for providing a viscosity-density product output signal indicative of the viscosity-density product of any fluid within said tube, said viscosity-density product output signal corresponding to the power required to sustain a predetermined angular amplitude of torsional mode oscillation of said tube with said fluid therein.

IN THE DRAWING

Figure 1:
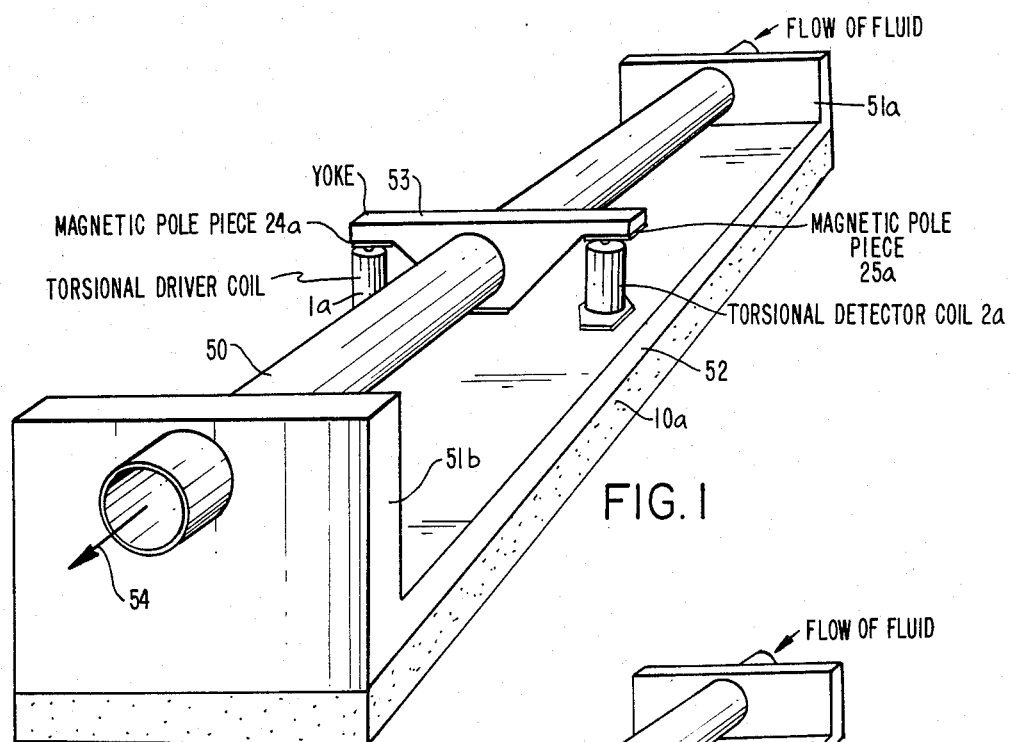
FIG. 1 is a perspective view of an in-line viscometer transducer according to a first embodiment of the present invention, for measurement of fluid viscosity.

In the drawing, those numerals which correspond to numerals in the drawing of copending U.S. patent application Ser. No. 483,142, filed Apr. 8, 1983, identify elements which are of similar construction and which perform similar functions.

DETAILED DESCRIPTION

Transducer Structure

Figure 2:
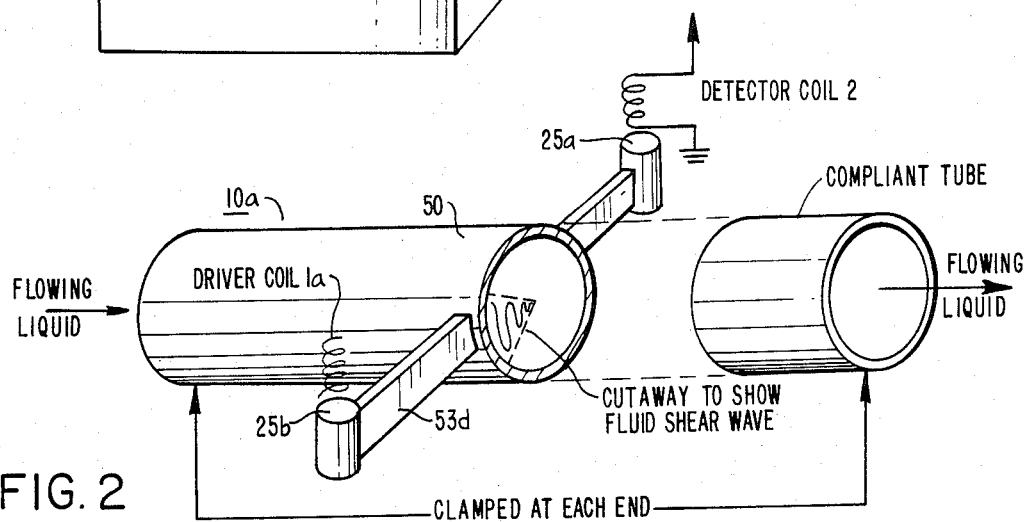
FIG. 2 is a partially cut-away perspective view of a modified form of said transducer.

The in-line viscometer transducer 10a shown in FIGS. 1 and 2 consists of a non-magnetic tube 50, preferably made of stainless steel and dimensioned to have sufficient torsional compliance and elasticity so that it can be maintained in torsional oscillation by the torsional driver coil 1a at a very small angular amplitude, typically on the order of about 0.001 radian, with very small internal energy loss in the tube itself when driven at the natural frequency of torsional oscillation of the tube.

The tube 50 is secured at each end by clamping or heliarc welding to the support blocks 51a and 51b, which are attached to a base plate 52. At the midpoint of the tube 50 between the support blocks 51a and 51b a non-magnetic yoke 53, preferably of stainless steel, surrounds the tube 50 and is secured to its periphery, preferably by heliarc welding.

The yoke 53 should be positioned at an antinode of oscillation of the tube 50. If the tube 50 is caused to oscillate in its fundamental mode, the antinode will be at the midpoint between the support blocks 51a and 51b. If, however, the tube 50 is caused to oscillate in its second harmonic mode, there will be two antinodes, each halfway between the midpoint of the tube 50 (between said support blocks) and the adjacent support block.

The yoke 53 extends transversely of the tube 50, and has a magnetic pole piece 25a secured to the bottom of one end and a magnetic pole piece 25b secured to the bottom of the other end. The electromagnetic driver coil 1a is mounted on the base plate 52 below the pole piece 25b, while an electromagnetic detector coil 2a is mounted on the base plate 52 below the pole piece 25a.

This arrangement allows the driver coil 1a to exert force on the pole piece 25b to cause the tube 50 to oscillate in torsion about its longitudinal axis 54; and causes the detector coil 2a to interact with the pole piece 25a to generate a signal having an amplitude and frequency corresponding to the amplitude and frequency of said torsional oscillation.

The circuitry which will be hereafter described provides a positive feedback loop between the detector and driver coils to maintain the tube 50 in torsional oscillation at a predetermined constant angular amplitude; and provides an output signal corresponding to the power provided to the driver coil 50, i.e. to the energy required to maintain the tube in oscillation at said predetermined angular amplitude.

When this is done, and a fluid is caused to flow through the tube 50 (with the fluid preferably filling the entire interior volume of the tube), the viscous resistance of the fluid is coupled to the internal wall of the tube by viscous friction forces and dampens the torsional vibration of the tube, so that additional power must be supplied to the driver coil 1a to maintain the tube at the predetermined amplitude of torsional oscillation, said power being a measure of the viscosity-density product of the fluid.

If the internal surface of the tube 50 is smooth, the viscous shear between the tube inner surface and the fluid within the tube is minimal, resulting in high precision of measurement but relatively low transducer sensitivity.

The sensitivity of the transducer 10a can be increased by roughening the internal surface of the tube 50 to increase the viscous shear applied to the fluid within the tube. This can be accomplished by abrasion of the tube surface or by stamping the tube to generate internal surface irregularities. Alternatively, a material having surface irregularities providing a large surface area, such as surgical cloth, can be secured to the internal surface of the tube. It is been found that such modifications can be made without adversely affecting the performance of the transducer.

It has also been found that the measured viscosity-density product is substantially independent of the flow rate of the fluid, for variations in flow rate of up to about 30%. The permissible variation in flow rate is greater for an internally smooth tube than for one which has been roughened, since there are turbulence effects in the latter case.

For greater precision of measurement, especially where there is a chance of trapping bubbles, the tube 50 should be maintained in a vertical position. Otherwise, the position of the tube 50 can be varied, with only a relatively minor effect on the measurement.

Figure 9:
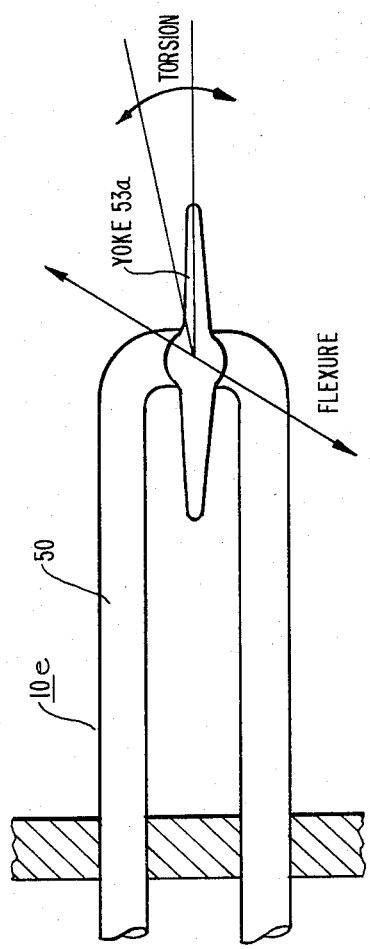
FIG. 9 is a side elevation view of an in-line viscometer transducer according to a fifth embodiment of the present invention.
Figure 10:
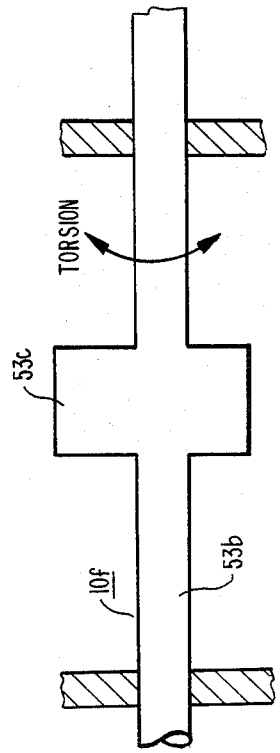
FIG. 10 is a side elevation view of an in-line viscometer according to a sixth embodiment of the present invention.

While the tube 50 is preferably straight and of circular cross-section, it may be curved and may have other (i.e. non-circular) cross-sections; or even a cross-section which varies along the length of the tube. For example, FIG. 9 shows a transducer 10e having a U-shaped tube 50a with a yoke 53a situated at the bend of the tube and in the plane thereof; and FIG. 10 shows a transducer 10f comprising a tube 53b having a central enlarged portion 53c.

As shown in FIG. 2, torsional oscillation of the tube 50 via the yoke 53d (which here consists of two separate pieces welded to opposite sides of the tube 50 so that the yoke extends along a diameter of the tube) generates a shear wave which propagates through the fluid within the tube toward the tube axis, with a shear rate equal to $$2\pi f \tag{1}$$

where $f_T$ = frequency of torsional oscillation

The torsional resonance frequency of a straight tube clamped or otherwise secured at both ends and twisted into torsional vibration by applying alternating torque at the midpoint of the tube between the clamped portions thereof, is equal to $$f_T = 2\pi (2K_T/I)^{\frac{1}{2}} \tag{2}$$

where $K_T$ = spring constant of the tube, i.e. the torque required to twist the tube through one radian at the midpoint between the clamped portions thereof $I$ = moment of inertia of the tube and yoke and $$K_T = G\pi(r_2^4 - r_1^4)/l \qquad (3)$$

where
G = modulus of rigidity of the tube material
$r_2$ = outer tube radius
$r_1$ = inner tube radius
l = length of tube between the clamped portions thereof
and $$I = \pi t \rho (r_2^4 - r_1^4)/2 \qquad (4)$$

where
t = thickness of tube wall
$\rho$ = density of tube material

The above equations assume the effect of the yoke to be negligible. Using equations 2 to 4, the torsional oscillation frequency of a one inch diameter empty type 316 stainless steel tube having a wall thickness of 0.85 mm. and a distance of 22.7 cm. between clamping points was calculated to be about 700 Hz.

In an actual test the resonant frequency of torsional oscillation of such a tube was found be be 635 Hz.

It has also been found that as the viscosity of the fluid within the tube increases, the resonant frequency of torsional oscillation decreases up to about 3%. However, this frequency change does not adversely affect the accuracy of the measurement of viscosity-density product.

Figure 7:
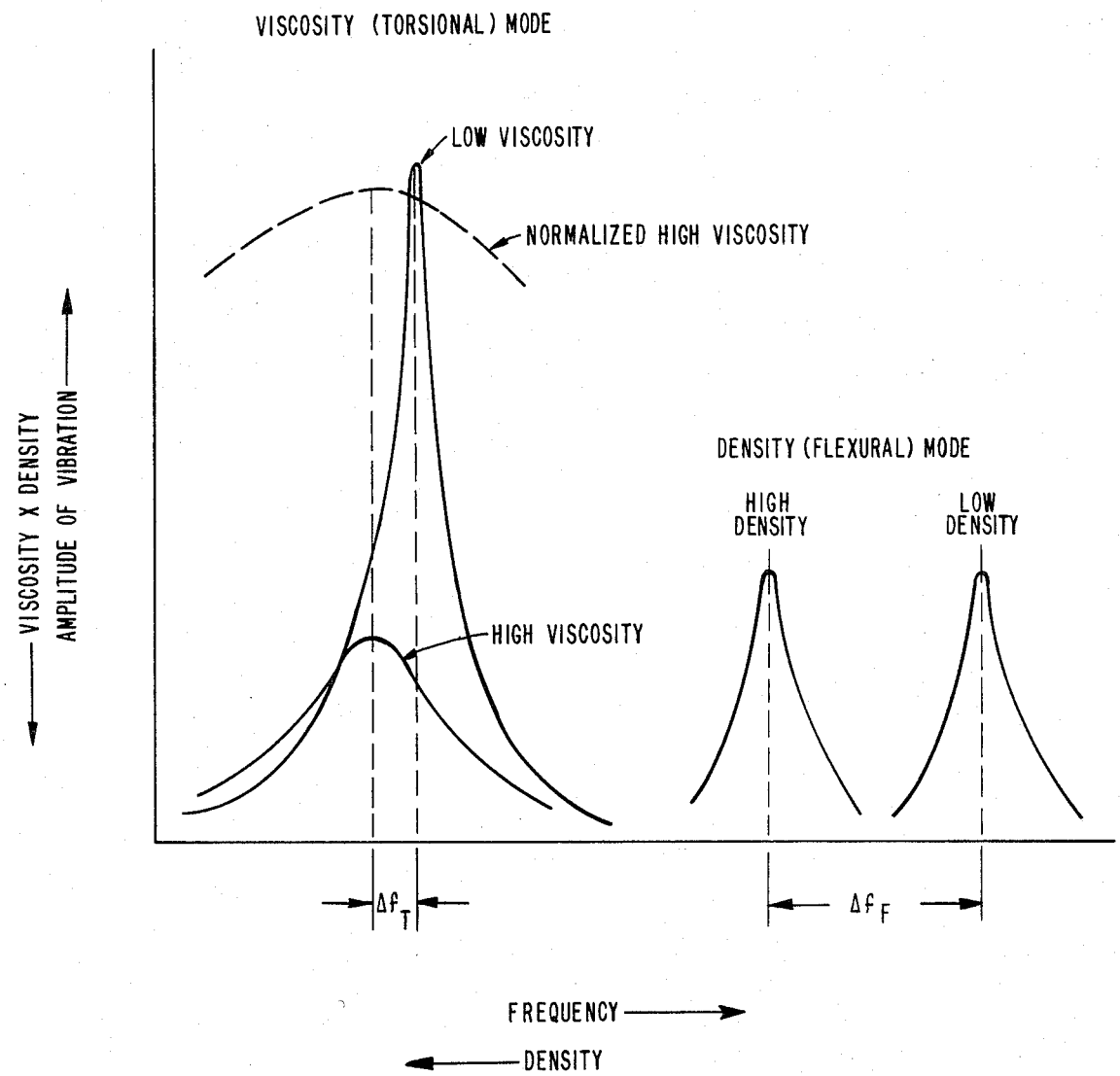
FIG. 7 is a graph useful in explaining the operation of the transducer and circuit of the invention.

The upper and lower left-hand curves in FIG. 7 show in solid lines the angular amplitude vs. frequency distribution for torsional oscillation of the tube 50 when filled with low viscosity and high viscosity fluids respectively, under conditions where the feedback circuit does not maintain the oscillation amplitude constant. It is evident that the frequency of torsional oscillation is slightly reduced as the fluid viscosity increases. The dashed line shows the angular amplitude vs. frequency distribution with the high viscosity fluid, using the control circuit 11 of FIG. 5, which maintains a constant amplitude of oscillation.

Figure 5:
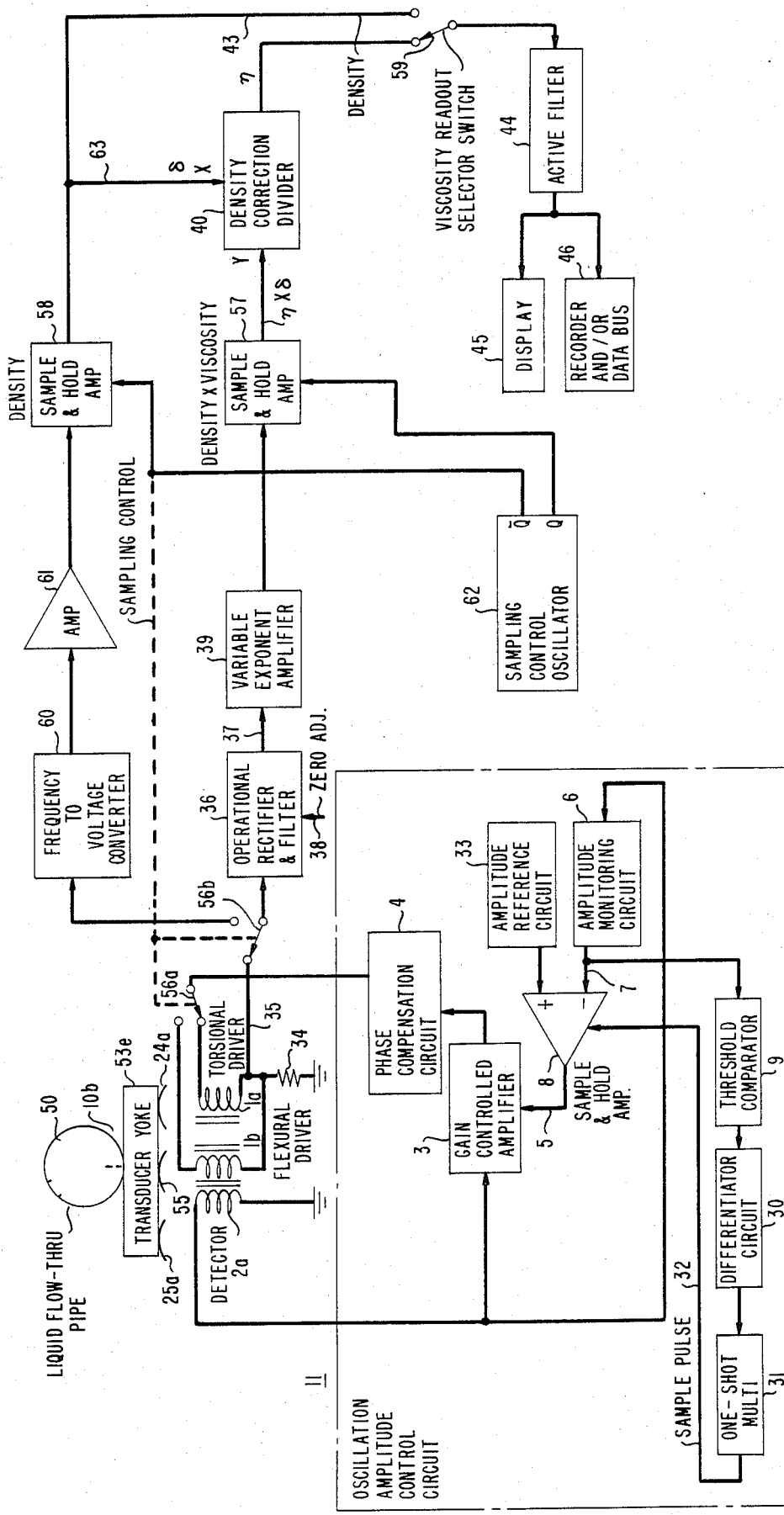
FIG. 5 is a functional block diagram of a viscometer-densitometer utilizing the transducer of FIG. 3 for alternately determining fluid viscosity and fluid density.

In an actual test of the transducer shown in FIG. 1 with the circuit shown in FIG. 5, the transducer having a stainless steel tube with a smooth internal wall surface, the sensitivity of the transducer was sufficient to enable the measurement of the viscosity-density product of water (nominally unity) with a resolution of $\pm 0.05$ centipoise $\times$ g/cm$^3$.

A high frequency of torsional oscillation is desirable for measuring the viscosity-density product of low viscosity liquids in order to obtain measurements comparable with measurements by capillary viscometers or rotary viscometers. The latter two types of viscometers generally operate at relatively low shear rates. Because low viscosity fluids usually are relatively shear independent, the higher frequency may be used. A higher frequency is desirable to simplify the electronic circuitry and mechanical construction of the apparatus. On the other hand, low frequency of torsional oscillation is desirable for shear thinning liquids in order to obtain measurements comparable with measurements of such liquids by capillary and rotary viscometers.

In order to minimize interference effects due to external vibration, the tube 50 should, if possible, be coupled into the fluid pipline at its ends by means of high compliance flexible sections of tubing. These flexible sections may comprise natural or synthetic rubber, or corrugated metal. It is also desirable to isolate the base plate 52 from its supporting structure by means of a resilient vibration absorbing material having high internal friction loss, such as foam rubber, acoustic absorption material, or the like.

If so desired, the drive coil 1a and magnetic pole piece 24a must be replaced by an electrostrictive or magnetostrictive element rigidly connected between the base plate 52 and yoke 53. Such structures would exhibit improved resistance to interference effects due to external vibrations.

Bimodal Transducer for Measurement of Fluid Density as well as Viscosity-Density Product It is generally known that the density of a fluid can be measured by causing flexural resonance of a tube (i.e. so that the tube axis bends) containing the fluid whose density is to be measured. Commercial densitometers based on this principle include the "Liquid Density Transmitter" made by Bell & Howell, Pasadena, Calif.; the "DPR 2000 On-line Density Measuring System" made by Anton Paar K. G., Graz, Austria; the "Vibration Type Liquid Density Measuring System" made by Yokogawa Electric Works, Tokyo, Japan; the "Dynatrol" made by Automation Products Co., U.S.A. The "E-Z Cal Density Gauge" sold by Texas Nuclear, Houston, Tex., measures density of the media flowing through a pipe by attenuation of radiation.

Such density gauges can be used to provide measurements for conversion of the viscosity-density product to provide true viscosity data. However, the arrangement hereafter described is capable of providing density data as well as viscosity data utilizing the same vibratory tube as has been described in the preceding portion of this specification.

The tube material should exhibit a relatively low coefficient of variation of elastic modulus with temperature. By providing a thermocouple or thermostat which generates an electrical signal corresponding to temperature, the density reading can be adjusted to compensate for the temperature variation in tube modulus of elasticity. The stainless steel tube hereafter described exhibited a flexural mode frequency shift of 0.06 Hz. per °C.

While isolation of the tube from external vibrations is not as critical for the flexural mode of vibration as for the torsional mode, the use of vibration isolation means similar to those employed in the torsional mode as described above, is preferred.

For a tube clamped at both ends the frequency of flexural resonance is given by $$f_F = 8(3EI/ml^3)^{\frac{1}{2}} \qquad (5)$$

where
E = the deflection modulus of the tube material
I = the area moment of inertia of the tube
m = mass of the tube per unit length
l = length of tube
and $$I = (d_2^4 - d_1^4)\pi/64 \qquad (6)$$

where
$d_2$ = outer diameter of tube
$d_1$ = inner diameter of tube

Using equations 5 and 6, the flexural resonance frequency for a one inch diameter empty type 316 stainless steel tube having a wall thickness of 0.85 mm. and a distance of 22.7 cm. between clamping points was calculated to be about 957 Hz; and a change of 7.0 Hz. corresponded to a fluid density change of about 0.33 g/cm$^3$. One experimental design of this type exhibited a flexural resonance frequency of 844 Hz., and a change of 10.1 Hz. corresponded to a fluid density change of about 0.33 g/cm$^3$. Since the resonant frequency can be accurately measured by available digital frequency measuring equipment, it is evident that the flexural resonance method described above is capable of very high resolution density measurements.

Figure 3:
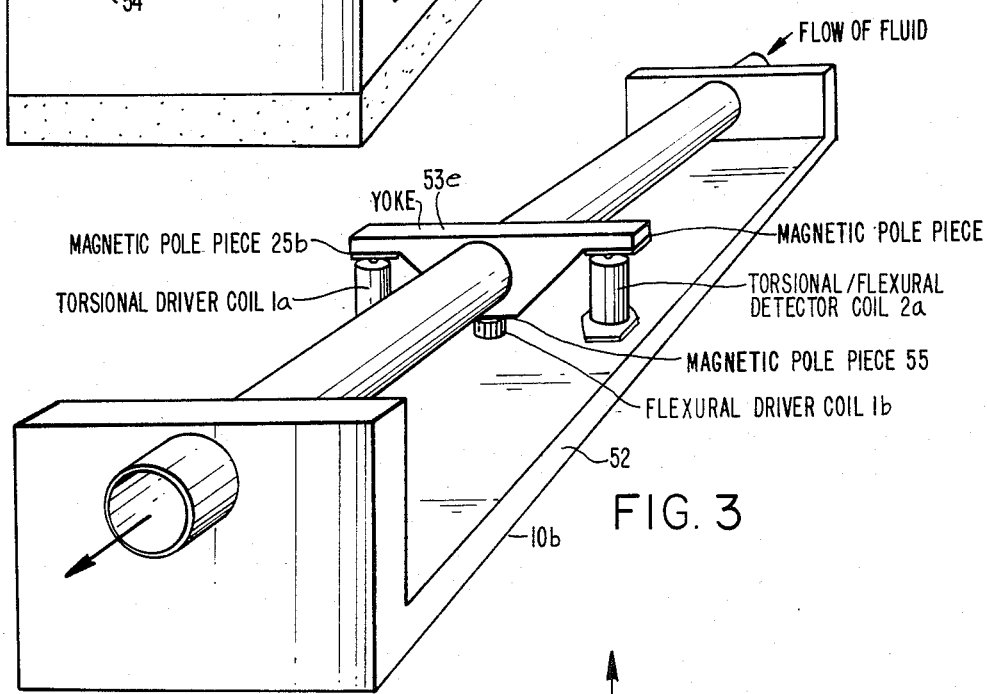
FIG. 3 is a perspective view of an in-line viscometer transducer according to a second embodiment of the invention, for alternate measurement of fluid viscosity and fluid density.

The transducer 10$b$ shown in FIG. 3 is a modified form of the transducer shown in FIG. 1, and is capable of sustained oscillation in either a flexural mode or a torsional mode.

The transducer 10$b$ is similar in construction to the transducer 10$a$ except for the yoke and the associated electromagnetic coils. In the transducer 10$b$ the driver coil 1$a$ and the detector coil 2$a$ are the same as those of the transducer 10$a$, and the detector coil 2$a$ serves to detect both torsional and flexural vibrations of the yoke 53$e$.

For optimum sensitivity, the detector coil 2$a$ should be a linear voltage characteristic differential transformer, since such devices exhibit relatively high sensitivity to small magnetic circuit element motions along the axis of their coils.

Instead of the detector coil 2$a$, other displacement or motion detectors, such as optical or capacitance detectors, may be employed.

A second driver coil 1$b$ is mounted on the base plate 52 below the yoke 52$e$ and tube 50, and vertically aligned with the axis of the tube 50, so that the magnetic pole piece 55 on the bottom of the central portion of the yoke 53$e$ interacts with the driver coil 1$b$ to cause the tube 50 to oscillate in a flexural mode, i.e. in a vertical plane. Alternatively, the driver coil 1$b$ and magnetic pole piece 55 may be replaced by an electrostrictive or magnetostrictive element connected between the base plate 52 and yoke 53$e$, so long as it exhibits sufficient lateral compliance to avoid inhibiting torsional vibration of the tube 50.

For measuring the viscosity-density product of the fluid within the tube 50, a positive feedback circuit is interconnected between the detector coil 2$a$ and the torsional driver coil 1$a$, and the power supplied to the driver coil 1$a$ in order to maintain a predetermined amplitude of torsional oscillation of the tube 50 is measured, as previously described with respect to the transducer 10$a$; said power being proportional to the fluid viscosity-density product.

For measuring the density of the fluid within the tube 50, substantially the same positive feedback circuit is interconnected between the detector coil 2$a$ and the flexural driver coil 1$b$, and the resonant frequency of flexural oscillation of the tube 50 is measured, said frequency being proportional to the fluid density. For maximum accuracy and stability of measurement, the amplitude of flexural oscillation should be kept constant—although amplitude variations have only a minor effect on the density measurement.

As shown in the two right-hand curves of FIG. 7, the difference in resonant frequency of flexural oscillation of the tube 50 for low density and high density fluids within the tube 50 is proportional to the difference in density of the fluids, the resonant frequency decreasing with increasing fluid density.

By using a sampling signal to switch back and forth between the torsional and flexural modes of oscillation of the tube 50, the transducer 10$b$ can be used to alternately measure both viscosity-density product and density. Preferably the switching rate should be no faster than about 5 seconds per cycle for fluids having a viscosity similar to that of water, to allow sufficient settling time for accurate measurements. A higher switching rate can be used for relatively low viscosity fluids, and a lower switching rate should be used for relatively high viscosity fluids.

In this alternate mode sample-and-hold circuits are employed to store the viscosity-density product and density information between successive readings thereof; and the viscosity-density product value is divided by the density value to provide a measurement of true viscosity of the fluid within the tube 50. The overall circuit for providing these functions is shown in FIG. 5.

Oscillation Control; Alternate Viscosity and Density Measurement Circuitry

As shown in FIG. 5, oscillation amplitude control circuit 11 causes the yoke 53$e$ and tube 50 to oscillate in torsion at a constant angular amplitude when the mode switch 56 (consisting of ganged sections 56$a$ and 56$b$) is in one position; and causes the yoke 53$e$ and tube 50 to oscillate in flexure at a constant linear amplitude when the mode switch 56 is in the other position.

In the torsional oscillation mode the current through the torsional driver coil 1$a$ and resistor 34 is proportional to the amplitude of torsional oscillation, and the square of said current, i.e. the square of the voltage developed across the resistor 34, corresponds to the power supplied to the driver coil 1$a$ to maintain the torsional oscillation amplitude, i.e. to the viscosity-density product of fluid within the tube 50. This product is determined by the operational rectifier and filter 36 and variable exponent amplifier squaring circuit 39, and stored in the sample-and-hold amplifier 57 between successive viscosity-density product readings. The density correction divider 40 uses a density signal from the density sample-and-hold amplifier 58 to divide the viscosity-density product signal from the amplifier 57 by density, so as to provide a true viscosity signal output on line 43, which viscosity signal may be coupled to the active filter 44 and display 45 or recorder and/or data bus 46 via readout selector switch 59.

In the flexural oscillation mode the current through flexural driver coil 1$b$ passes through resistor 34, and the corresponding voltage signal (having a frequency corresponding to the density of the fluid within the tube 50) is converted by the frequency to voltage converter 60 (which may be a suitably calibrated frequency counter or a frequency discrimnator circuit) to a signal corresponding to fluid density. This density signal is amplified by the amplifier 61 and stored in the sample-and-hold amplifier 58 between successive density readings; from which amplifier the density signal is used to convert the viscosity-density signal from the sample-and-hold amplifier 57 to true viscosity and/or to provide a density readout via the readout selector switch 59, as previously described.

The sampling control oscillator 62, comprising an astable multivibrator or clock, alternately switches the circuit between the torsional (viscosity-density product determining) and flexural (density determining) oscillation modes, by switching the ganged switch sections 56a and 56b and simultaneously alternately enabling the sample-and-hold amplifiers 57 and 58. The sampling rate can be varied by varying the frequency of the oscillator 62.

In the oscillation amplitude control circuit 11, gain controlled amplifier 3 has its input connected to the output of detector coil 2a and its output connected through a phase compensation circuit 4 to the input of driver coil 1a or 1b, to form a positive feedback loop which maintains the tube 50 in torsional or flexural oscillation at the natural frequency thereof. The amplitude of the oscillation is maintained constant by control of the gain of amplifier 3 via a gain control signal applied thereto on line 5.

An amplitude monitoring circuit 6 has its input connected to the output of detector coil 2a, and provides on its output line 7 an AC signal at the frequency of oscillation of the tube 50, said AC signal having an amplitude corresponding to the amplitude of oscillation of the tube 50.

The AC signal output of amplitude monitoring circuit 6 is applied to (i) sample-and-hold circuit 8 and (ii) threshold comparator 9. Threshold comparator 9 generates an output signal once during each cycle of the AC signal on line 7, at a time when said AC signal crosses a preset amplitude threshold, i.e. at a time when yoke 53e (i.e. tube 50) is in a particular position of its cycle of (torsional or flexural) oscillation, preferably at or near the peak of the oscillation cycle. That is, the output signal from threshold comparator 9 always appears in successive cycles at the same physical position of the yoke 53e.

Threshold comparator 9 includes a 90° phase shift circuit to shift the AC signal on line 7 so that the zero crossovers of the phase shifted signal occur at the same times as the peaks of said AC signal on line 7. The comparator 9 then compares the phase shifted signal with ground, to generate an output signal at each positive-going (or negative-going) zero crossover.

The output of threshold comparator 9 is differentiated by differentiator circuit 30, with the output of circuit 30 being coupled to monostable multivibrator 31, which provides sampling pulses (one sampling pulse per cycle of oscillation of the tube 50) to the sample-and-hold circuit 8 on line 32.

The AC signal on line 7, corresponding to amplitude of oscillation of the tube 50, is compared by sample-and-hold circuit 8 with a DC reference signal (indicative of the desired amplitude of oscillation of the tube 50) provided by amplitude reference circuit 33, the comparison being made only at times corresponding to the appearance of sampling pulses on line 32.

The result of each such amplitude comparison, i.e. the amplitude error signal, is stored by sample-and-hold amplifier 8 and held at the last stored value between successive samples, so that the output of amplifier 8 is a verying DC amplitude error signal which is applied to gain controlled amplifier 3 to maintain the amplitude of oscillation of the yoke 53e (and therefore of tube 50) at a predetermined constant value.

In order to prevent overloading of the sample-and-hold amplifier 8 due to transients caused, e.g., by shock to the transducer assembly 10b, a clipping circuit (not shown) prevents the output of the sample-and-hold amplifier 8 from exceeding a preset value in the negative direction and from rising above zero volts in the positive direction.

In remote monitoring and process control applications, the transducer 10b may be installed a considerable distance from the oscillation amplitude control circuit 11, so that the lines to the coils 1a, 1b and 2a may be rather long, with typical line lengths being as much as 350 ft. The phase shift introduced by these lines changes the loop phase shift between coils 1a or 1b and 2a (nominally 180°) required for proper oscillatory operation of the transducer 10b, so that oscillation of the tube 50 and yoke 53e is intermittent and, in severe cases, ceases entirely.

To overcome this problem and enable operation with long lines between transducer 10b and control circuit 11, a phase compensation circuit 4 introduces an adjustable amount of phase shift into the positive feedback loop. The phase compensation circuit 4 is adjusted so that the transducer 10b oscillates properly with close to 180° phase shift between the drive and detector coils 1a or 1b and 2a under varying load conditions (e.g. with the tube 50 filled with fluids having viscosities in the range of 0.001 to 2,000 poise), and the viscosity output signal on line 43 exhibits acceptable long term stability.

With the transducer 10b oscillating in the torsional mode under control of the circuit 11, an AC signal having an amplitude nominally corresponding to the square root of the viscosity-density product of the fluid within the tube 50, is provided from resistor 34 on line 35, this signal corresponding to the current flowing through the drive coil 1a, which is in series with resistor 34.

The AC signal on line 35 is converted to a DC signal having a value corresponding to the current through resistor 34, by operational rectifier and filter 36; the output of rectifier and filter 36 appearing on line 37, said output being shifted by a DC zero adjust level applied on line 38 to compensate for internal losses in the transducer 10b, i.e. to calibrate the viscometer to zero viscosity when the tube 50 is filled with air or vacuum.

The variable exponent amplifier 39 "squares" the output signal on line 37, since the viscosity-density product is proportional to the power supplied to the drive coil 1a, which in turn is proportional to the square of the current through the resistor 34. Since in a real circuit the relationship between the signal on line 37 and viscosity-density produce is not a perfect square function, the variable exponent amplifier 39 has an adjustable exponent range on the order of 1.9 to 2.1. This circuit has been found to provide an excellent linearity of output of viscosity-density product.

A suitable variable exponent amplifier is available from Analog Devices, Norwood, Mass., as a "Model 433 Programmable Multi-Function Module".

A density correction circuit 40 divides the viscosity-density product output of variable exponent amplifier 39 by a density signal from the density sample-and-hold amplifier 58 on line 63. The output signal from density correction circuit 40 on line 43 is then a DC signal corresponding to the viscosity of the fluid within the tube 50. A suitable divider circuit is Analog Devices, Inc. AD 535, using two trims as described in Analog Devices Data Acquistion Products Catalog Supplement, page 59S (1979).

The viscosity output signal on line 43 is then applied to an active filter comprising RMS to DC converter 44, which accurately averages out noise due, e.g., to pipeline turbulence and other sources. Such RMS to DC converters are commercially available from various sources, including National Semiconductor Corporation and Analog Devices, Inc.

Applicants have found that the RMS to DC converter 44 works better than other types of active filters in smoothing viscosity and density signals. The reason for this improvement in performance is not known. In addition, the RMS to DC converter responds more quickly to changes in the viscosity signal or the density signal than do other types of filters, and has less overshoot.

The viscosity or density signal output of the RMS to DC converter 44 is coupled to a digital display 45 and, if desired, to a recorder or a data transmission bus 46.

If desired, the drive coils 1a and 1b may each comprise a pair of coils disposed on opposite sides of the same portion of the yoke 53e, and driven in push-pull arrangement by a complementary symmetry amplifier.

The detector coil 2a may be similarly constructed, resulting in cancellation of common mode noise; which arrangement is particularly advantageous when the lines to the coils 1a, 1b and 2a are long.

Simultaneous Bimodal Determination of Viscosity and Density

While the circuit shown in FIG. 5 determines both fluid viscosity and fluid density by alternately operating the transducer 10b in a torsional oscillation mode (for viscosity determination) and in a flexural oscillation mode (for density determination), it is possible to determine both viscosity and density simultaneously by causing the tube 50 to oscillate in both the torsional and flexural modes at the same time.

It has been found that cross-coupling between the torsional mode and the flexural mode of oscillation of the tube 50 is small, and is negligible for most measurements. Therefore simultaneous operation in both modes can be realized by means of two separate sets of driver and detector coils, namely (i) a driver coil for causing only torsional oscillation of the tube 50 and a detector coil responsive only to said torsional oscillation, and (ii) a second driver coil for causing only flexural oscillation of the tube 50 and a second detector coil responsive only to said flexural oscillation. One such transducer arrangement is shown in FIG. 4a and another such arrangement is shown in FIG. 4b, the arrangement of FIG. 4b being preferred.

Figure 4A:
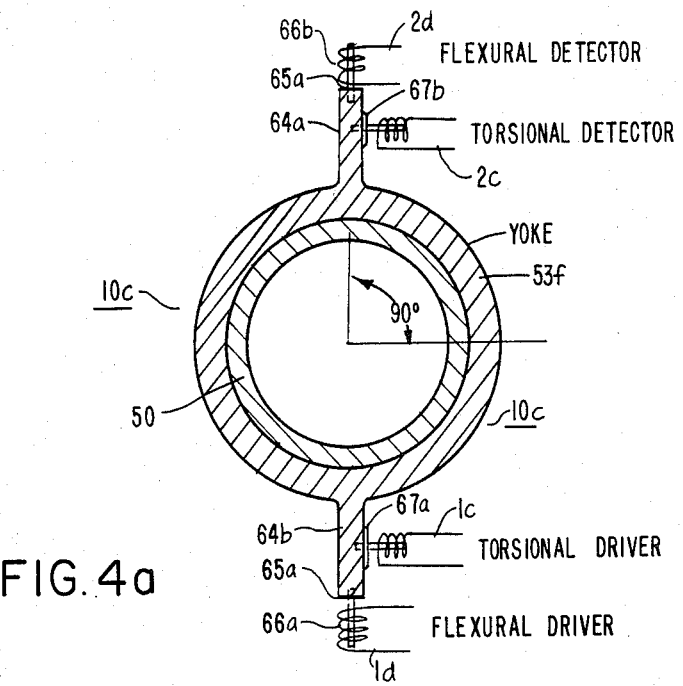
FIG. 4a is a cross-sectional view of an in-line viscometer transducer according to a third embodiment of the present invention, capable of simultaneously determining both fluid viscosity and fluid density.
Figure 4B:
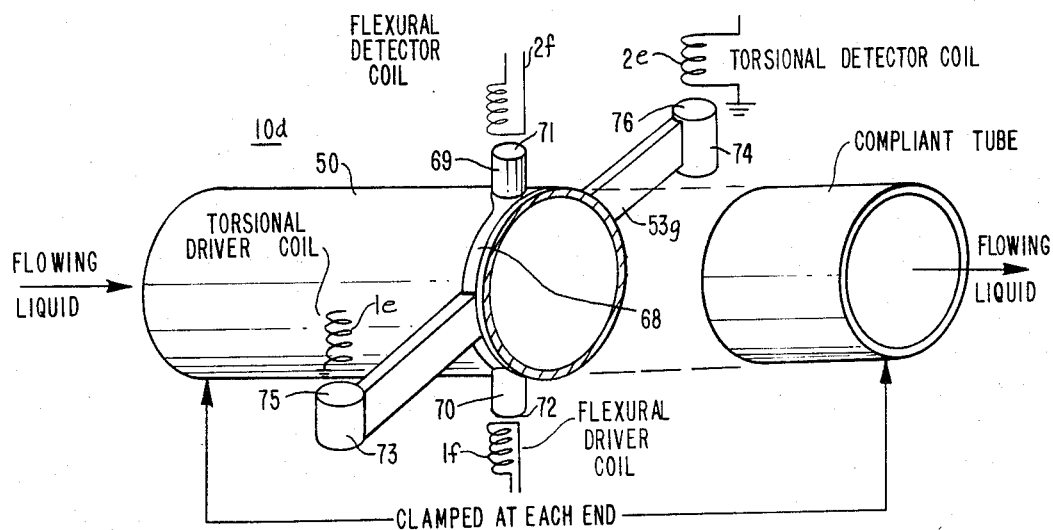
FIG. 4b is a partially cut-away perspective view of an in-line viscometer transducer according to a modified third embodiment of the present invention, capable of simultaneously determining both fluid viscosity and fluid density.

In FIG. 4a, the yoke 53f has the form of a flanged cylinder which surrounds the tube 50, with the upper and lower flanges 64a and 64b preferably lying in a vertical plane through the axis of the tube 50. The flanges 64a and 64b have flexural mode driver and detector magnetic pole pieces 65a and 65b respectively, extending from the free ends of the flanges, for cooperating with the adjacent flexural driver and flexural detector coils 66a and 66b respectively, to cause the tube 50 to oscillate in a flexural mode in a vertical plane.

The flanges 64a and 64b also have torsional mode driver and detector magnetic pole pieces 67a and 67b respectively, extending laterally from the flanges, for cooperating with the adjacent torsional driver and torsional detector coils 1c and 2c respectively, to cause the tube 50 to oscillate in a torsional mode. The yoke 53f may be constructed of a material similar to that of the yoke 53e, and may be secured to the tube 50 by welding, shrink fitting, or any other suitable method yielding a strong joint exhibiting low internal friction under vibration conditions. The flexural and torsional detectors 2d and 2c are preferably linear voltage characteristics differential transformers.

In the transducer 10c of FIG. 4a, the various coils must be carefully positioned to minimize cross-talk between the torsional and flexural modes of oscillation, and hence between the viscosity-density product and density determining circuits.

Such cross-talk can be reduced, and the coil adjustment rendered less critical, by the transducer arrangement shown in FIG. 4b, wherein the transducer 10d has a yoke 53g comprising a cylindrical collar 68 surrounding the tube 50. The collar 68 may be of a similar material to that of the yokes 53e and 53f, and may be secured to the tube 50 in similar fashion.

Protruding vertically upwardly and downwardly from the collar 68 of the yoke 53f in the plane of the axis of the tube 50 are upper and lower cross-arms 69 and 70 respectively, with corresponding upper and lower magnetic pole pieces 71 and 72 disposed at the end of each of said cross-arms respectively.

Protruding laterally from the collar 68 are left and right cross-arms 73 and 74 respectively, with corresponding left and right upwardly facing magnetic pole pieces 75 and 76 disposed adjacent the end of each of said cross-arms respectively.

A torsional driver coil 1e cooperates with the pole piece 75, while a torsional detector coil 2e cooperates with the pole piece 76. A flexural driver coil 1f cooperates with the pole piece 70, while a flexural detector coil 2f cooperates with the pole piece 71.

Since the torsional and flexural coils of the transducer 10d of FIG. 4b are on separate cross-arms and are spaced further apart than the torsional and flexural coils of the transducer 10c of FIG. 4a, the transducer 10d exhibits lower cross-talk than the transducer 10c.

Figure 6:
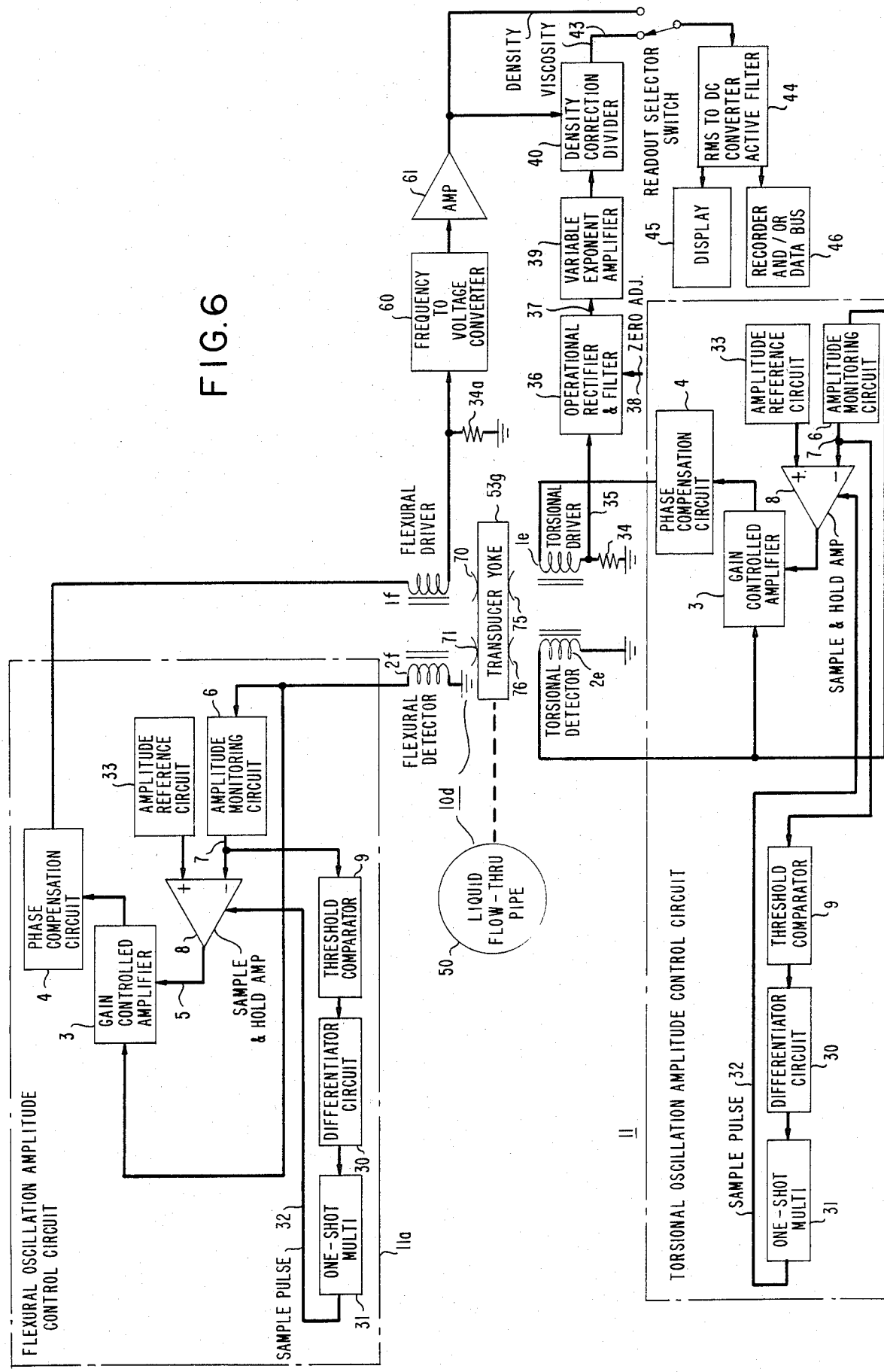
FIG. 6 is a functional block diagram of a viscometer-densitometer utilizing the transducer of FIG. 4a or FIG. 4b for simultaneously determining viscosity and density.

The circuit for simultaneous measurement of fluid viscosity-density product and fluid density using the transducer 10d, is shown in FIG. 6 and operates in essentially the same manner as the circuit shown in FIG. 5, except that no switching between oscillation modes is done, and the circuit 11 is used to maintain a constant amplitude of torsional oscillation, while a substantially identical circuit 11a (differing from the circuit 11 only in particular circuit adjustments to reflect the difference in values attributable to flexural vs. torsional oscillation) is used to maintain a constant amplitude of flexural oscillation, said circuits maintaining oscillation of the tube 50 at its resonant frequencies for torsional and flexural oscillation respectively.

In FIG. 6 all elements having the same numbers as elements in FIG. 5 are of the same construction and function in the same manner, with a signal having an amplitude corresponding to the square root of fluid viscosity-density product being developed across resistor 34; and a signal having a frequency corresponding to fluid density being developed across resistor 34a. Thus a detailed description of FIG. 6 is not necessary.

Figure 8:
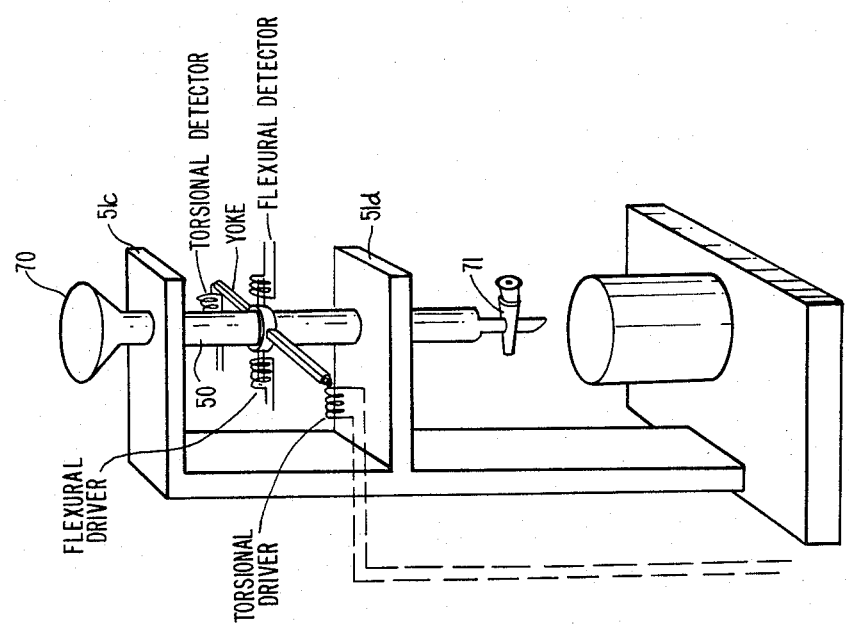
FIG. 8 is a perspective view of an in-line viscometer transducer according to a fourth embodiment of the present invention and suitable for laboratory usage.

The laboratory viscometer-densitometer shown in FIG. 8 operates in the same manner as the transducer 10d shown in FIG. 4d. In the laboratory instrument, however, the tube 50 is vertically oriented and is held in position by the upper and lower support blocks 51c and 51d. The fluid sample is poured into the tube 50 via the funnel 70; and can be removed via the stopcock 71.

Any driver coil and its associated pole piece can be replaced by an electrostrictive or magnetostrictive element connected between the transducer yoke and the transducer base plate or another stationary supporting member. Any detector coil and its associated pole piece can be replaced by any other suitable detector, e.g. of optical, capacitive or piezoelectric type.

We claim:

1. A transducer assembly for an in-line vibratory viscometer, comprising:
   a tube exhibiting elasticity, through which tube a fluid may flow;
   means for securing first and second longitudinally spaced sections of said tube to provide oscillation nodes at said sections;
   a transverse yoke secured to a third section of said tube intermediate said first and second sections thereof;
   drive means comprising means operatively associated with said yoke for exciting and maintaining a torsional mode of oscillation of said tube beween said nodes, said drive means also including independently controllable means operatively associated with said yoke for exciting and maintaining a flexural mode of oscillation of said tubes between said nodes;
   torsional detector means for detecting said torsional oscillation;
   means coupled to said drive means and said torsional detector means for providing a viscosity-density product output signal indicative of the viscosity-density product of any fluid within said tube; and
   flexural detector means responsive to the flexural oscillation of said tube.

2. A transducer assembly for an in-line vibratory viscometer, comprising:
   a tube exhibiting elasticity;
   means for securing first and second longitudinally spaced sections of said tube to provide oscillation nodes at said sections;
   a transverse yoke secured to a third section of said tube intermediate said first and second sections thereof;
   drive means comprising means operatively associated with said yoke for simultaneously exciting and maintaining torsional and flexural modes of oscillation of said tube between said nodes;
   torsional detector means for detecting said torsional oscillation;
   means coupled to said drive means and said torsional detector means for providing a viscosity-density product output signal indicative of the viscosity-density product of any fluid within said tube; and
   flexural detector means responsive to the flexural oscillation of said tube.

3. The transducer assembly according to claim 1 or 2, wherein said drive means includes at least one stationary electromagnetic element and a cooperating magnetically permeable member coupled to said tube for oscillation therewith.

4. The transducer assembly according to claim 1 or 2, wherein said tube has a roughened internal surface portion between said first and second sections thereof.

5. The transducer assembly according to claim 1, wherein said detector means comprises at least one stationary detector coil and a cooperating magnetically permeable member coupled to said tube for oscillation therewith.

6. The transducer assembly according to claim 1, wherein said drive means is coupled to one end of said yoke and said detector means is coupled to the other end of said yoke.

7. The transducer assembly according to claim 1, wherein said drive means is coupled to a region of said tube in a plane extending midway between the ends of said yoke.

8. The transducer assembly according to claim 2, wherein said drive means comprises:
   an electromagnetic flexural drive coil and a cooperating magnetically permeable member adjacent said yoke for causing said tube to flexurally oscillate in deflection about the longitudinal axis of the tube;
   an electromagnetic torsional drive coil and a cooperating magnetically permeable member adjacent said yoke for causing said tube to rotationally oscillate in torsion about said longitudinal axis;
   a first detector coil responsive only to the flexural oscillation of said tube; and
   a second detector coil responsive only to the torsional oscillation of said tube.

9. The transducer assembly according to claim 8, wherein said flexural drive coil is physically disposed in quadrature with said torsional drive coil, and said first detector coil is physically disposed in quadrature with said second detector coil.

10. The transducer assembly according to claim 1, further comprising means coupled to said drive means and said detector means for providing a viscosity-density product output signal indicative of the viscosity-density product of any fluid within said tube, said output signal corresponding to the power required to sustain a predetermined angular amplitude of torsional oscillation of said tube with said fluid therein.

11. The transducer assembly according to claim 1, further comprising means coupled to said drive means and said detector means for providing an output signal indicative of the density of any fluid within said tube, said output signal corresponding to the natural frequency of flexural oscillation of said tube with said fluid therein.

12. The transducer assembly according to claim 1, wherein said viscosity-density product output signal correspond to the power required to sustain a predetermined angular amplitude of torsional mode oscillation of said tube with said fluid therein;
   means coupled to said drive means and said detector means for providing a density output signal indicative of the density of any fluid within said tube, said density output signal corresponding to the natural frequency of flexural mode oscillation of said tube with said fluid therein; and
   means for providing a true viscosity signal indicative of the viscosity of said fluid, by dividing the value of said viscosity-density product signal by the value of said density signal.

13. The transducer assembly according to claim 1 or 2, wherein said tube is U-shaped between said nodes.

14. The transducer assembly according to claim 1 or 2, wherein said tube has an enlarged portion between said nodes, said drive means and said detector means being coupled to said enlarged portion.

15. The transducer assembly according to claim 1 or 2, wherein said drive means comprises an electrostrictive or magnetostrictive member connected between a stationary member and said yoke.

16. The transducer assembly according to claim 1 or 2, further comprising first circuit means connected between said drive means and said detector means for providing a torsional oscillation mode control signal to said drive means to maintain said tube in torsional oscillation at substantially the natural frequency thereof and at a predetermined constant amplitude; and second circuit means for generating a viscosity-density product indicating signal corresponding to the power of said torsional oscillation mode drive signal supplied by said first circuit means to said drive means.

17. The transducer assembly accoring to claim 16, wherein said first circuit means includes means for adjusting the phase shift between the output signal from said detector means and the torsional oscillation mode input signal to said drive means, to compensate for transmission line length variations between said tube and said first circuit means.

18. A transducer assembly for an in-line vibratory viscometer, comprising:

a tube exhibiting elasticity;

means for securing first and second longitudinally spaced sections of said tube to provide oscillation nodes at said sections;

a transverse yoke secured to a third section of said tube intermediate said first and second sections thereof;

drive means comprising means operatively associated with said yoke for exciting and maintaining oscillation of said tube between said nodes, said drive means comprising:

flexural drive means for causing said tube to flexurally oscillate in deflection about the longitudinal axis of the tube, torsional drive means for causing said tube to rotationally oscillate in torsion about said longitudinal axis, flexural detector means responsive to the flexural oscillation of said tube, torsional detector means responsive to the torsional oscillation of said tube, and means coupled to said torsional drive means and said torsional detector means for providing a viscosity-density product output signal indicative of the viscosity-density product of any fluid within said tube.

19. The transducer assembly according to claim 18, wherein the same elements constitute said flexural detector means and said torsional detector means.

20. The transducer assembly according to claim 18, wherein said flexural drive means and said flexural detector means are disposed on opposite sides of said tube along a first line extending through the tube axis; and said torsional drive means and torsional detector means are disposed on opposite sides of said tube along a second line extending through the tube axis, said second line being perpendicular to said first line.

21. The transducer assembly according to claim 1, 2 or 18, further comprising vibration isolation means for reducing coupling of external vibrations to said transducer assembly.

22. An in-line vibratory viscometer, comprising:
a transducer having:
a tube extending elasticity, through which a fluid may flow means for securing first and second longitudinally spaced sections of said tube to provide oscillation nodes at said sections, a transverse yoke secured to a third section of said tube intermediate said first and second sections thereof, drive means comprising means operatively associated with said yoke for exciting and maintaining torsional oscillation of said tube between said nodes, and detector means for detecting said torsional oscillation;

first circuit means connected between said drive means and said detector means for providing a torsional oscillation mode control signal to said drive means to maintain said tube in torsional oscillation at substantially the natural frequency thereof and at a predetermined constant amplitude; and second circuit means coupled to said drive means and said detector means for providing a viscosity-density product output signal indicative of the viscosity-density product of any fluid within said tube, said viscosity-density product output signal corresponding to the power required to sustain a predetermined angular amplitude of torsional mode oscillation of said tube with said fluid therein.

23. The viscometer according to claim 22, further comprising:

flexural drive means operatively associated with said yoke for exciting and maintaining flexural oscillation of said tube between said nodes;

flexural detector means for detecting said flexural oscillation;

means coupled to said flexural drive means and said flexural detector means for providing a density output signal indicative of the density of any fluid within said tube, said density output signal corresponding to the natural frequency of flexural mode oscillation of said tube with said fluid therein.

24. The viscometer according to claim 23, further comprising means for providing a true viscosity signal indicative of the viscosity of said fluid, by dividing the value of said viscosity-density product signal by the value of said density signal.

* * * * *